United States Patent
Rahn et al.

(10) Patent No.: US 8,041,783 B2
(45) Date of Patent: Oct. 18, 2011

(54) METHOD FOR DISTRIBUTION OF CONFIGURATION SETTINGS FOR MEDICAL DEVICES

(75) Inventors: Norbert Rahn, Forchheim (DE); Gudrun Zahlmann, Neumarkt (DE); Markus Schmidt, Nuremberg (DE); Ali-Nejat Bengi, Erlangen (DE); Horst Schreiner, Fuerth (DE)

(73) Assignee: Siemens Aktiengesellschaft, Munich (DE)

( * ) Notice: Subject to any disclaimer, the term of this patent is extended or adjusted under 35 U.S.C. 154(b) by 770 days.

(21) Appl. No.: 11/408,916

(22) Filed: Apr. 20, 2006

(65) Prior Publication Data
US 2007/0250832 A1    Oct. 25, 2007

(51) Int. Cl.
*G06F 15/177* (2006.01)
(52) U.S. Cl. ........ 709/220; 709/221; 709/222; 709/223; 717/171; 717/176; 717/177; 717/170; 705/2
(58) Field of Classification Search .......... 709/217–219, 709/220–222, 223; 717/168, 170–174, 176–178; 705/2
See application file for complete search history.

(56) References Cited

U.S. PATENT DOCUMENTS

| | | | |
|---|---|---|---|
| 5,666,645 A * | 9/1997 | Thomas et al. | 725/47 |
| 6,598,011 B1 * | 7/2003 | Kucek et al. | 702/185 |
| 7,054,823 B1 | 5/2006 | Briegs et al. | |
| 7,287,257 B2 * | 10/2007 | Meza | 719/321 |
| 2002/0010618 A1 * | 1/2002 | Pellegrinelli et al. | 705/10 |
| 2003/0208378 A1 * | 11/2003 | Thangaraj et al. | 705/2 |
| 2004/0059597 A1 | 3/2004 | Tkaczyk et al. | |
| 2005/0038673 A1 * | 2/2005 | Stookey et al. | 705/2 |
| 2005/0149869 A1 * | 7/2005 | Kehr et al. | 715/700 |
| 2005/0192837 A1 * | 9/2005 | Fears et al. | 705/2 |
| 2006/0173713 A1 * | 8/2006 | Petro et al. | 705/2 |
| 2006/0178189 A1 * | 8/2006 | Walker et al. | 463/16 |
| 2007/0010719 A1 * | 1/2007 | Huster et al. | 600/300 |
| 2007/0100585 A1 * | 5/2007 | Dulberg et al. | 702/184 |
| 2008/0052505 A1 * | 2/2008 | Theobald | 713/1 |
| 2008/0220848 A1 * | 9/2008 | Adiraju et al. | 463/20 |

* cited by examiner

*Primary Examiner* — Kenneth R Coulter
(74) *Attorney, Agent, or Firm* — Schiff Hardin LLP

(57) ABSTRACT

A method is provided for configuring medical devices such as medical devices used in a clinical trial. Based on the needs of the clinical trial, a definition of a configuration of the medical devices to be used in the clinical trial is generated and the configuration data is transformed into a profile. The profile is distributed to sites at which the clinical trial will be conducted and the profile is applied to the medical devices at the sites to configure the medical devices. The medical devices are thereby capable of producing data that is comparable as between the sites used in the clinical trial.

6 Claims, 1 Drawing Sheet

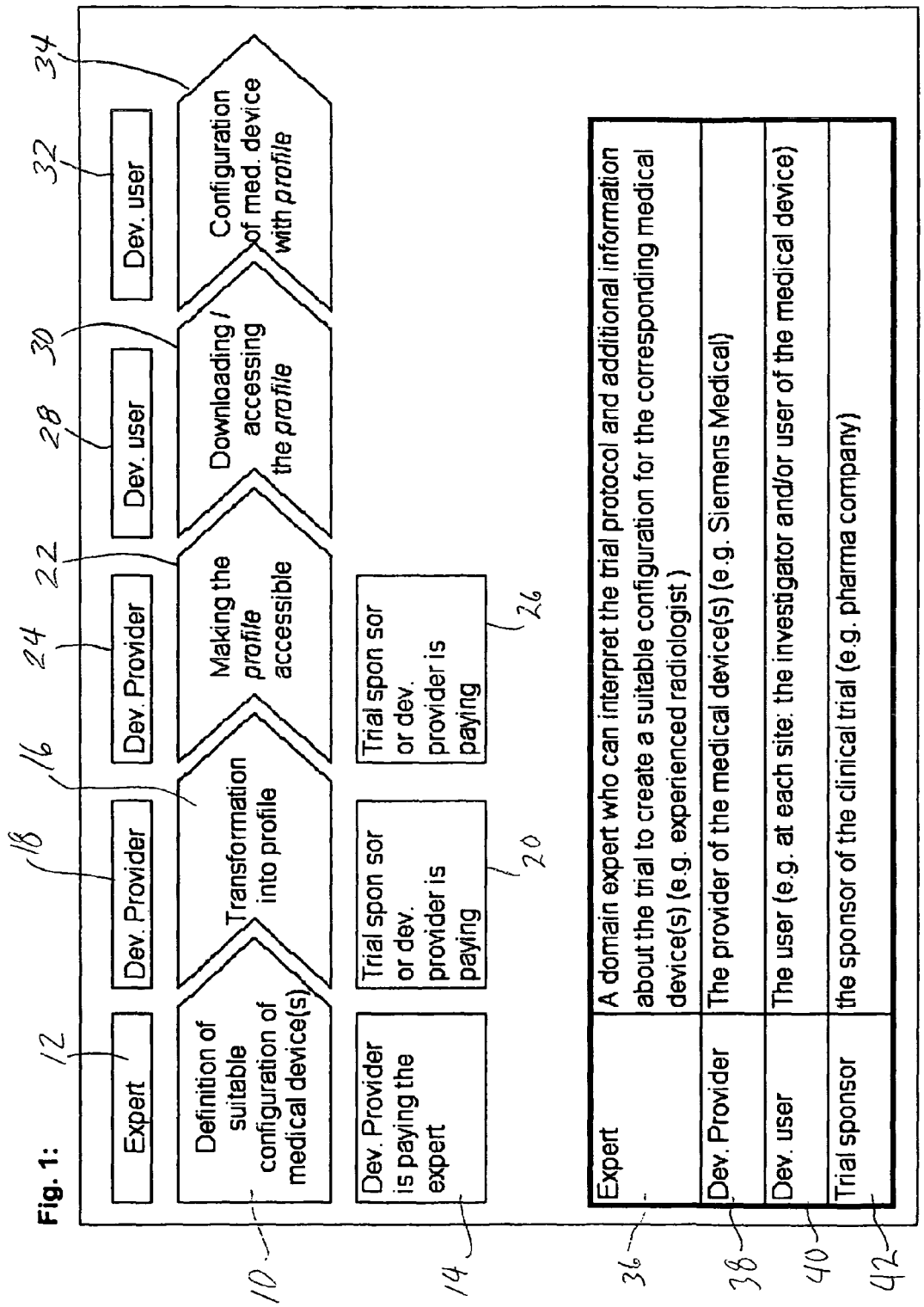

METHOD FOR DISTRIBUTION OF CONFIGURATION SETTINGS FOR MEDICAL DEVICES

BACKGROUND OF THE INVENTION

1. Field of the Invention

The present invention relates generally to a method for distributing configuration settings for electronic devices and in particular to distribution of configuration settings for medical devices.

2. Description of the Related Art

Medical devices are becoming increasingly complex and the possibilities for configuring the medical devices to perform their various functions are likewise becoming increasingly more complex. For example, the medical devices may have signal recording settings and the imaging settings, for example, that may be configured. This allows for the maximum adaptability of the medical devices to the needs of the physicians, radiologists, etc. The needs of the individual medical professional and the experience of the medical professional influence the configuration settings of the medical device that are applied. This results in a large variety of configurations of the medical devices as used by different physicians and users of the medical devices.

Clinical trials rely on standardized data acquisition in order to achieve comparable results. In the case of medical trials which are conducted at various locations, also referred to as multi-centric trials, these various sites often have different medical devices. The quality of the clinical trial relies on the data acquisition process being the same, and the configuration of the medical device that obtains the data plays a substantial role in ensuring that the data is comparable.

Up to now, clinical trials have generally been conducted at more than one site and the data acquired using the medical devices is very likely to have been acquired from the medical devices which are configured differently from one another. The medical devices might be from the same vendor or from different vendors. Representatives of the various sites for the clinical trial, which typically may include investigators and/or users of the medical devices such radiologists or the like, generally get together and discuss the data required for the clinical trial. These representatives must translate these data requirements into configurations that are specific to the medical devices at the sites. This results in differences in the configurations. In order for the data from the medical devices to be comparable, reliance must be made on the experience and judgment of the users of the medical devices.

SUMMARY OF THE INVENTION

The present invention provides a method for solving one or more of the problems described above. In general, a profile is generated which automatically changes the settings of the medical devices so as to generate comparable data. The profile is distributed to the sites for the clinical trial and applied to the medical devices. The resulting data from the clinical trial may thereby be compared across the different sites at which the trial is conducted without concern that the data is affected by different settings and configurations for the medical devices that obtained the data.

BRIEF DESCRIPTION OF THE DRAWINGS

FIG. 1 is a schematic representation of a process for generating and distributing a profile for medical devices for use in configuring the medical devices for clinical trials and the like.

DETAILED DESCRIPTION OF THE PREFERRED EMBODIMENTS

With reference to FIG. 1, a definition of a suitable configuration of the medical devices, as indicated at 10, is identified by an expert 12. The protocol of the clinical trial and the corresponding information is provided to the expert 12. This effort is paid for by the sponsor of the clinical trial. As indicated in FIG. 1, the device provider may pay the expert as indicated at 14.

The information about the configuration is transformed into a profile as indicated at 16. The profile is electronically storable information and can be used to automatically change the settings of medical devices of the same kind from different vendors if there is a standardized method to set the configuration with a standardized profile. The profile can also be used to automatically change the settings of a medical device from the same vendor if there is a method to set the configurations with a profile. The device provider 18 is generally responsible for this step. Here, the trial sponsor or the device provider pays for the transformation into the profile, as indicated at 20.

In the following step, the profile information is made accessible, as indicated at 22. This step is generally performed by the device provider as indicated at 24 and is paid for by the trial sponsor or the device provider as indicated at 26. The step of making the profile accessible as indicated at 22 may be carried out by providing the profile using the Internet. The profiles may either be sent out to the sites or may be provided at a site to which the other sites are provided access such as by the users of the medical devices. Alternatively, the profile can be distributed using the communication channels of the clinical trial such as via networks, by inclusion of recordable media having the profile, with packages of materials for the trial, or by other means.

In the following step, the device user as indicated at 28 performs a download or an access of the profile at 30. Subsequently, the device user, here indicated at 32, performs a configuration of the medical device with the profile, as indicated at 34.

Since the clinical trial will be performed at a number of different sites using different medical devices, the steps 30 and 34 will be performed at each of the sites involved in the clinical trial.

The lower portion of FIG. 1 identifies the players in the method. The expert 36 is an expert in the domain or technology area who can interpret the trial protocol and the additional information about the clinical trial to create a suitable configuration for the corresponding medical devices which will be used. Examples of experts are experienced radiologists, doctors and the like. The device provider 38 is another player in the method and is the provider of the medical devices which are used in the clinical trials. An example of a device provider is Siemens Medical. A device user 40 is the user of the medical device at each site. The device user may be an investigator in the clinical trial or an end user at the medical facility, clinic or hospital where the medical device is located. The trial sponsor 42 is the entity which sponsors the clinical trial, such as a pharmaceutical company or other interested entity.

The advantages achieved by the present method are that the data acquired from the different sites in a clinical trial, where a clinical trial is conducted at more than one site, is collected from each site with a single profile for the configuration of the medical devices used to collect the data. The utilization of the same configuration for the medical devices allows for better comparability of the data sets from each site and thus has a direct impact on the quality of the clinical trial.

Thus, there is shown and described a method for configuring medical devices to provide comparable data for instance in a clinical trial so that the data gathered is of a higher quality.

Although other modifications and changes may be suggested by those skilled in the art, it is the intention of the inventors to embody within the patent warranted hereon all changes and modifications as reasonably and properly come within the scope of their contribution to the art.

We claim:

1. A method for configuring medical devices, comprising the steps of:
   generating a profile of configuration data for a plurality of medical devices to be used in a clinical trial, said configuration data configuring the plurality of medical devices to produce test data meeting requirements of the clinical trial, said plurality of medical devices being mutually different from one another, said step of generating said configuration profile including:
      defining a configuration of the medical devices for a predetermined task; and
      transforming said configuration into said configuration profile;
   distributing said profile of configuration data over a network to user sites having the medical devices;
   applying said configuration profile to the medical devices at said user sites to automatically configure the medical devices to output data meeting requirements for the clinical trial; and
   operating the medical devices according to the configuration profile to generate data for the clinical trial.

2. A method as claimed in claim 1, wherein said step of distributing said configuration profile is performed via the Internet.

3. A method as claimed in claim 1, wherein said step of distributing said configuration profile is performed along communication channels of a clinical trial.

4. A method for generating data in a clinical trial, comprising the steps of:
   defining a configuration of a plurality of mutually different medical devices suitable to needs of the clinical trial;
   transforming said configuration into a configuration profile;
   distributing said configuration profile over a network to sites of the clinical trial;
   automatically configuring said plurality of mutually different medical devices at the sites to output data meeting requirements of the clinical trial by applying the configuration profile to the medical devices; and
   conducting the clinical trial using data output by the medical devices configured according to said configuration profile.

5. A method for distributing configuration data for medical devices, comprising the steps of:
   defining a configuration of a plurality of the medical devices, said plurality of medical devices being mutually different devices;
   transforming said configuration into a configuration profile;
   distributing said configuration profile over a network to sites having said medical devices; and
   applying said configuration profile to said plurality of medical devices at said sites to automatically configure the medical devices to produce medical data meeting predetermined requirements so as to be capable of being compared between the medical devices.

6. A method for distributing configuration data for medical devices, comprising the steps of:
   defining a configuration for a plurality of the medical devices to be used in a clinical trial, said plurality of medical devices being mutually different devices;
   transforming said configuration into a configuration profile for the plurality of medical devices so that the plurality of medical devices are configured to produce test results meeting the requirements of the clinical trial;
   distributing said configuration profile over a network to sites having said plurality of medical devices;
   applying said configuration profile to the plurality of medical devices at said sites to automatically configure said plurality of medical devices to produce medical data meeting predetermined requirements so that the data are capable of being compared between the medical devices; and
   operating the medical devices according to the configuration profile to generate data for the clinical trial.

* * * * *